United States Patent [19]
Hilblom

[11] 3,954,010
[45] May 4, 1976

[54] VISUAL AND ELECTRONIC BATTERY HYDROMETER

[75] Inventor: Richard W. Hilblom, Tinley Park, Ill.

[73] Assignee: Illinois Tool Works Inc., Chicago, Ill.

[22] Filed: Apr. 25, 1975

[21] Appl. No.: 571,896

[52] U.S. Cl. .................................. 73/291; 73/293; 73/447
[51] Int. Cl.² ..................... G01N 9/18; G01F 23/02
[58] Field of Search ............ 73/444, 447, 327, 291, 73/293; 116/118 R; 136/182

[56] References Cited
UNITED STATES PATENTS

| | | | |
|---|---|---|---|
| 3,498,141 | 3/1970 | Nelson et al. | 73/327 X |
| 3,570,311 | 3/1971 | Nelson | 73/327 |
| 3,597,972 | 8/1971 | Ryder | 73/291 |
| 3,597,973 | 8/1971 | Ryder | 73/291 |
| 3,777,574 | 12/1973 | Brown et al. | 73/453 |
| 3,834,235 | 9/1974 | Bouton et al. | 73/293 |
| 3,844,171 | 10/1974 | Rodger | 73/293 |
| 3,893,339 | 7/1975 | Melone | 73/327 |

*Primary Examiner*—Richard C. Queisser
*Assistant Examiner*—Joseph W. Roskos
*Attorney, Agent, or Firm*—J. R. Halvarsen; R. W. Beart

[57] ABSTRACT

A combined visual and electronic liquid indicator which may be used as a battery hydrometer is disclosed. An outer housing of a generally cylindrical shape receives a centrally located elongated light transmitting viewing rod. The lower portion of the rod extends into a channel at the lower end of the outer housing. A float is retained in the channel by a retaining cage. A second generally cylindrical inner member which fits over the rod and into the outer housing has a light sensor and a light detector secured at its lower end across diametrically opposite portions of the float channel, and the outer housing and the inner member are then sealed together.

4 Claims, 7 Drawing Figures

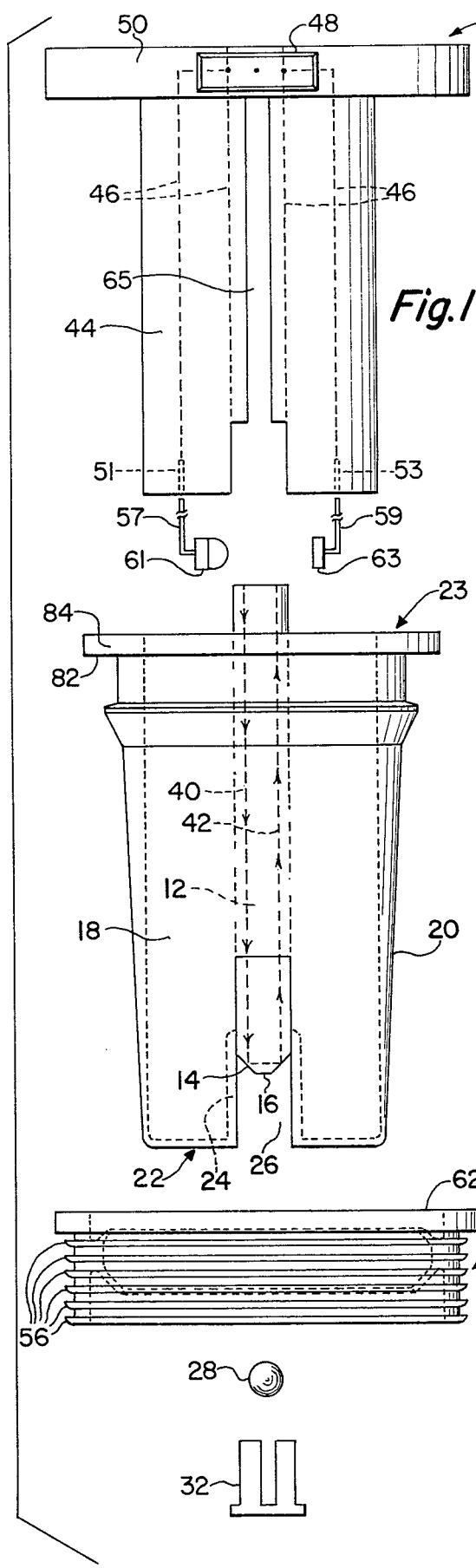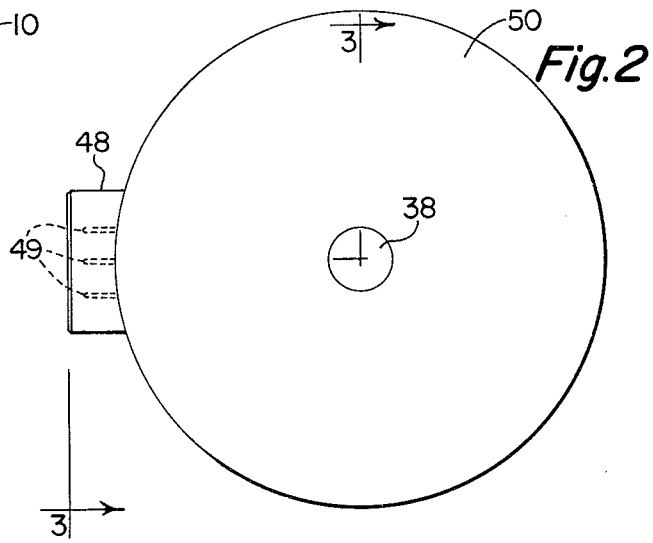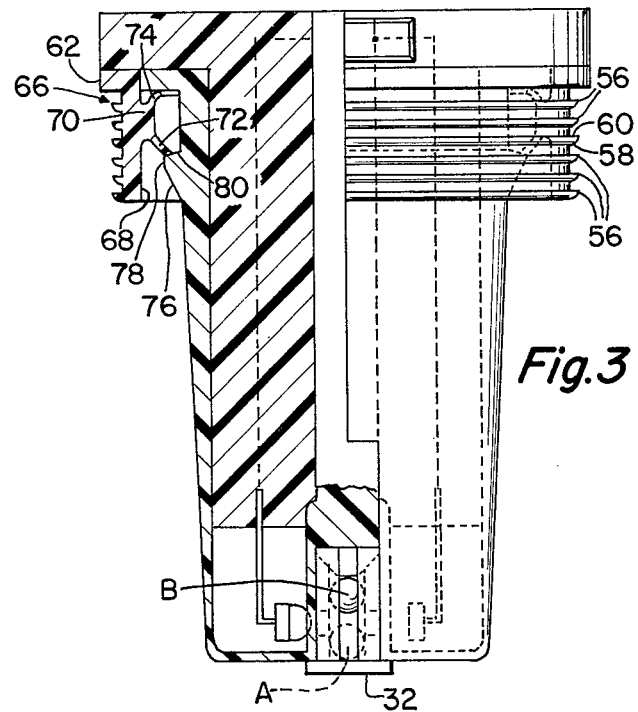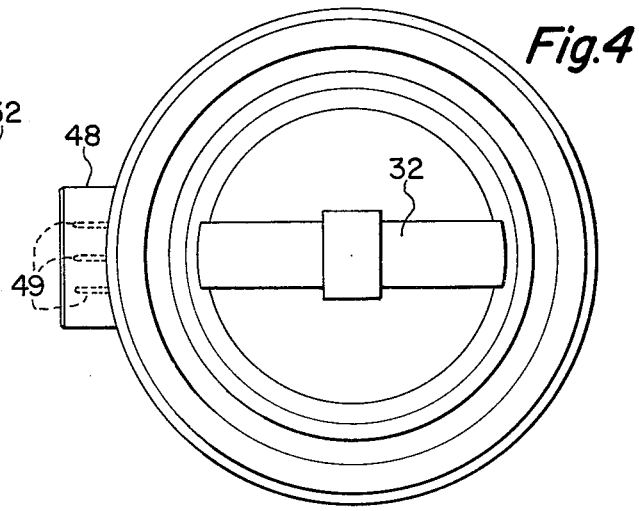

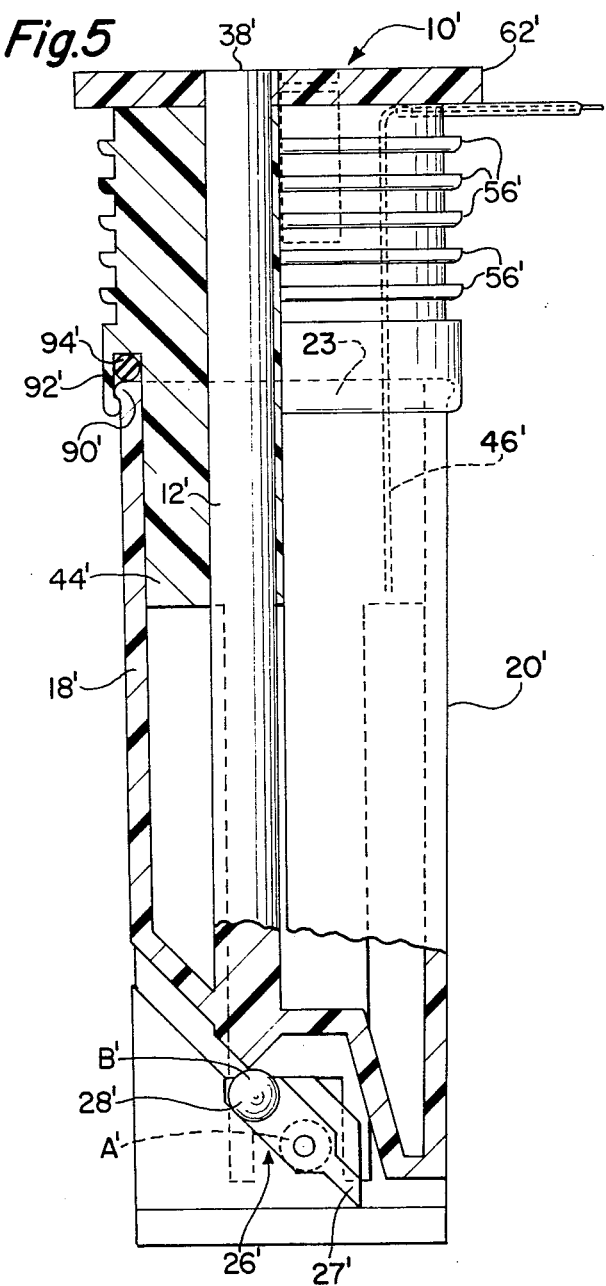
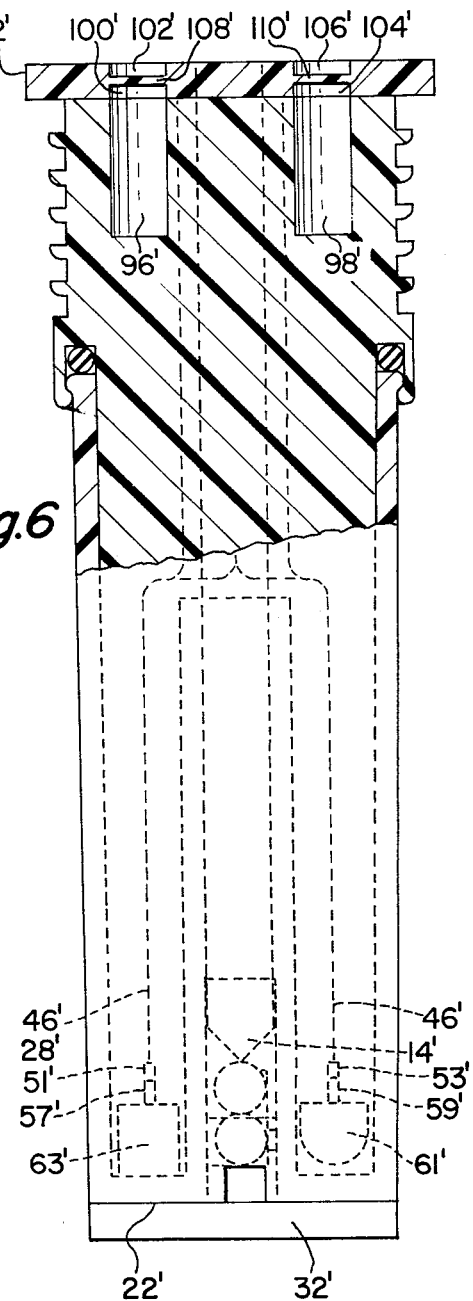
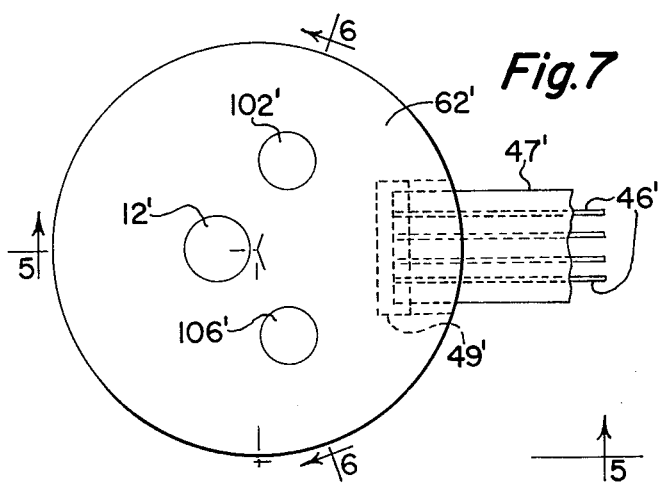

VISUAL AND ELECTRONIC BATTERY HYDROMETER

BACKGROUND OF THE INVENTION

Visual hydrometers which indicate the liquid level and the specific gravity of a liquid are well known for many applications, including checking of storage batteries. The simplest manner in which this is achieved is by use of an elongated light transmitting view rod which has a conical lower end that extends into a channel which contains a float. The float is generally a ball of a bright color so that when it is adjacent the conical end of the viewing rod the observer looking down at the top surface of the rod will see the colored float. Thus, when the observer sees the float it indicates to him that the liquid level is adequate and that the specific gravity of the liquid is appropriate. If the float falls in the channels sufficiently far below the conical end of the rod so that it may no longer be viewed, it indicates to the observer that the liquid level is low when a bright indication is presented or that the specific gravity of the liquid is low when a dark indication is presented.

Electronically monitored hydrometers are also known in which a light beam between a light source and a light detector are interrupted by a float. A conventional manner of implementing such a system is to mount the light source and the light sensor in a part of a cap which extends above the liquid, and to transmit the light down one light pipe to a reflector which reflects the light across a channel in the liquid that contains the float to a second reflector which directs the light up a second light pipe to a light detector. The position of the float determines whether the light beam is interrupted so that the liquid level or the specific gravity of the liquid may be electronically monitored at a remote location.

The difficulty of sealing the sensor and the light source in an electronic hydrometer from the liquid being sensed has encouraged the aforementioned construction in which the light source and detector are positioned at a location which is removed from the liquid. This construction results in a bulkier configuration for the hydrometer and requires additional parts such as the light pipes and the reflecting prisms, thereby noticeably increasing the cost of the unit. Moreover, while prior electronic liquid monitoring indicators were capable of lighting a warning light, such as a light on the dash board of an automobile, to indicate that its battery was not operating properly, these indicators did not provide for a way of checking whether or not the electronic monitoring system was itself operating properly. Moreover, prior electronic liquid monitoring indicators required electrical current from the battery in order to operate. When a faulty battery was present in a vehicle which would not start at all, the electronic monitoring system of the vehicle became useless unless it was supplied from an auxillary power source. With the advent of sealed batteries, the task of locating the source of a battery failure became even more difficult. However, with the combined visual and electronic indicator of the present invention, even a sealed battery may be checked visually. Other advantages of the hydrometer of the present invention are that the light detector may be positioned so that it is directly in line with the light source, thereby allowing a less intense light source and lower power dissipation, and that the light source and light detector are sealed from the liquid being monitored by an outer housing which supports the visual viewing rod.

DESCRIPTION OF THE DRAWINGS

The present invention is described by reference to the drawings in which:

FIG. 1 is an exploded side view of one embodiment of the present invention which utilizes a snap-on collar that seals the inner member and the outer housing of the indicator;

FIG. 2 is a top view of the indicator of FIG. 1;

FIG. 3 is a side partial cross-section of the view of the indicator of FIG. 1 and FIG. 2 taken along the lines 3—3 of FIG. 2;

FIG. 4 is a bottom view of the indicator of FIG. 1;

FIG. 5 is a partial cross-section of an alternate version of the indicator of the present invention taken along the lines 5—5 of FIG. 7;

FIG. 6 is a partial cross-section of the view of the indicator along the lines 6—6 of FIG. 7; and FIG. 7 is a top view of the indicator of FIGS. 5 and 6.

TECHNICAL DESCRIPTION OF THE INVENTION

An exploded view of one version of the combined visual and electronic liquid level indicator 10 of the present invention is shown in FIG. 1. The visual indication for the liquid level indicator of FIG. 1 is provided by an elongated light transmitting viewing rod 12 which has a conical lower end 14 that may either by pointed or terminated by a horizontal flat surface, such as surface 16. The rod 12 may be formed of a light transmitting material such as acrylic, styrene or other clear or partially clear materials. The rod 12 is retained in a generally cylindrically shaped outer housing 18, the outer walls 20 of which slope inwardly slightly as they approach the closed lower end 22 of the housing 18 from the open upper end 23 of the housing. A small hub 24 is formed in the central area of the lower end 22 of the housing 18 in order to receive the conical lower end 14 of the rod 12 therein. A channel 26 is formed in the hub 24 and in the lower portion of the housing wall 20 which is open to the liquid environment on the sides of the housing that face the viewer in FIG. 1. A float, which is preferably a ball 28 of an elastomeric substance, is positioned in the channel 26. A retaining cage 32 is secured across the bottom of the channel 26 to retain the ball 28 in place into the channel 26.

An assembled unit consisting of the housing 18, the viewing rod 12, the float ball 28 and the retaining cage 32 may be utilized as a completed visual viewing structure. With this structure, a person who wishes to check the liquid level or specific gravity of the liquid may look into the upper surface 38 of the rod 12. The light entering this surface would then travel down along the line 40 and would be reflected up along the line 42 if the level of the liquid in the battery, or other container, being checked is low since the float ball 28 in this case will be at the position A indicated in FIG. 3. When the ball 28 is in this position a yellow or bright indication will be presented to the viewer of the surface 38 because the liquid level will also be below the conical end 14 of the rod 12. When the conical portion 14 of the rod 12 is immersed in the liquid, the liquid is at the proper level in the battery, the viewing indication at the surface 38 will depend on whether or not the ball 28 is at the position A or at the position B. If the ball is at the position B of FIG. 3, the specific gravity of the liquid is adequate and the ball is visible so that a viewer will see a color indication corresponding to the color of the ball 28. On the other hand, if the specific gravity is low but the liquid level is adequate, the ball will fall from position B to position A while liquid remains around the lower conical end 14 of the rod 12. The light which enters the surface 38 is then refracted by the surrounding liquid so that a dark indication appears at the surface 38.

The unit thus far described may be utilized as a separate visual indicator independently of the remaining portions of the indicator if desired. Thus, another advantage of the indicator of FIGS. 1-4 is that the same parts may be utilized to construct either a simple visual indicator or a combined visual and electronic liquid level indicator. If it is desired to complete the structure in order to provide a combined visual and electronic battery indicator, the inner member 44, which is of a generally cylindrical shape and is constructed so as to fit into the interior of the outer housing 18, is positioned into the housing 18 so as to receive the rod 12 in its centrally located channel 65. Molded-in electrical conductors 46 extend through the member 44 to terminals 49 in a plug 48 which projects from the cover 50 of the member 44. Female connecting pins 51, 53 are secured in the lower end of the member 44 to receive the male connecting pins 57, 59 of the light source 61 and the light detector 63 respectively.

After the inner member 44 has been inserted into the outer housing 18 and the float ball 28 is secured in place in the channel 26 by the retaining cage 32, a positive seal must be provided to seal the housing members 18 and 44 against leakage of liquid into the area of the light source 61 and the light detector 63. In the present invention, this is provided by means of the collar 52 which in addition provides a way in which the entire unit may be secured into an aperture in the container wall of a battery, or other liquid container. The sealing collar 52 is shown in more complete detail in U.S. patent application Ser. No. 452,086 filed in the name of Robert Melone, which application is also assigned to the assignee of the present invention.

The embodiment of the present invention, shown in FIGS. 1-4, is especially adapted for measuring the level and specific gravity of the electrolyte of sealed batteries having a liquid container that has a large central aperture which leads into the battery. The collar 52 secures the indicator 10 in the container when it is pressed downwardly into the aperture in the battery container. The collar 52 is preferably formed of a somewhat resilient plastic material such as polypropylene and it has a plurality of ribs 56 which have upwardly curved lower surfaces 58 and a flat upper surface 60. The curved surfaces 58 allow the collar 52 to be depressed into the aperture in the (not shown) container so as to be tightly secured thereto, but so as to resist removal from the container once the collar 52 has been forced into place. The upper rim 62 of the collar 52 then fits over the upper surface of the container.

The collar 52 is secured to the outer housing 18 to seal against loss of liquid from the battery and the admission of external liquids into the battery and the inner member 44 by means of an integrally formed sealing element 66 which extends inwardly towards the outer periphery of the housing 18 from the inner surface 68 of the collar 52. The sealing element 66 extends in an annular manner around the entire inner surface 68 and is formed with a relatively rigid downwardly projecting sealing member 72 and a relatively flexible upwardly projecting sealing member 74, both of which preferably have an annular shape. The housing 18 has an outwardly inclined relatively wide surface 76 which extends to a short vertical transition surface 78. The transition surface 78 meets with a relatively short inwardly inclined surface 80.

To complete the assembly of the indicator structure the collar 52 is inserted over the bottom of outer housing 18. The collar 52 is slid upwardly until the rigid sealing member 72 is deflected outwardly by the surface 76 and is then snapped into place against the inwardly inclined surface 80. When the rigid sealing member 72 is pressed against the surface 80, so as to form a seal therebetween, the flexible sealing member 74, because of its length, will be bent inwardly against the lower surface 82 of the disc 84 which extends outwardly from the top of the housing 18 so as to provide an upper seal to prevent the passage of gas or liquid between the collar 52 and the housing 18, thereby sealing off the light source 61 and the light detector 63 from the liquid being measured.

The electronic indication of the present indicator 10 results from the use of the float ball 28 as a shutter between the light source 61 and the light detector 63. For example, when the ball 28 is at position B shown in FIG. 3, light will be transmitted from the light source 61 to the light detector 63, thereby providing a signal at the terminals 49 that indicates the battery is in a satisfactory operating condition. If the electrolyte level is low or if the specific gravity of the electrolyte is low, the ball will drop to the position A and thereby block light traveling from the light source 61 to the light detector 63 so as to provide an indication to the remote circuitry that a defective battery condition exists.

An alternate version of a visual and electronic liquid level indicator in accordance with the present invention is shown in FIGS. 5-7. Electrical connections to the male connecting pins 57', 59' of the light source 61' and the light detector 63' are made by means of the wires 46' which are covered by a flexible insulating cover 47' that passes through the slot 49' in the cover disc 62', and then down through the channel (not shown) in the inner member 44' to the female connecting pins 51', 53' which mate with the male connecting pins 57', 59'.

The indicator 10' of FIGS. 5-7 differs from the indicator of FIGS. 1-4 in that the ribs 56' are integrally molded on the inner member 44' which is positioned in the outer housing 18'. Also, the side wall 20' is tapered and terminates in an annular upper locking rim 90' near the open end 23' of the housing 18' which engages a downwardly projecting annular locking rim 92' of the inner member 44'. An O-ring 94' is compressed between the locking rim 90' and the locking rim 92' to provide a seal between the outer housing 18' and the inner member 44'. The light source 61' and the light detector 63' are secured to the lower end of the inner member 44'. The float ball 28' is retained in channel 26' with the retaining cage 32' being located near the closed end 22' of the outer housing 18', and extending across the entire lower surface of the outer housing 18'. The channel 26' has a small opening 27' at its lower end which allows for the free flow of the liquid being monitored.

Another difference of the version shown in FIGS. 5-6 is that the channel 26' for the float ball 28' is inclined with respect to the vertical so that the ball 28' will be at the position B shown in FIG. 5 when the liquid level and the specific gravity of the electrolyte is satisfactory and the ball 28 will be at the position A' when either the liquid level or the specific gravity of the liquid is low. Use of an inclined channel 26' insures that the ball 28' will not be viewed when the specific gravity of the electrolyte is low.

Another feature of the embodiment of FIGS. 5–7 is the addition of a pair of cylindrical bores 96', 98' in the upper part of the inner member 44'. Corresponding recesses 100' and 102' and 104' and 106' in the cover disc 62' overlie the bores 96' and 98' respectively. The recesses 100' and 102' in the cover disc 62' are separated by the thin wall 108', while the recesses 104' and 106' are separated by the thin wall 110'. These recesses are provided so that if the walls 108', 110' are punctured a pair of bores are formed through the cover disc 62' into the inner member 44'. These bores allow for the insertion of screws, or other removal member, therein so that the indicator 10' may be pulled out of an aperture in a container against the resistance provided by the ribs 56' in order to salvage the unit, or at least the light source 61' and the light detector 63'. The ribs 56' generally provide such a good seal that removal of the indicator 10' from the battery or other container is very difficult without damaging it. If the bores 96' and 98' are formed in the member 44', the indicating rod 12' is offset from the center of the cover disc 62', as shown in FIG. 7.

What is claimed is:

1. A combined direct visual and remote liquid condition indicating device comprising a container means having an open end, a closed end which is insertable into the liquid to be monitored and a channel which extends towards said open end of said container means from said closed end; a float retained in said channel, an inner member having an exterior shape that is configurated so as to generally conform to the interior shape of said container means, a light source and a light detector secured to said inner member on opposite sides of said channel in alignment with each other so that said float acts as a shutter therebetween in accordance with the level and specific gravity of the liquid that is being monitored, said light source and said light detector being positioned adjacent said closed end of said container means, an elongated light transmitting direct viewing rod secured to said container means and having a conical shaped end portion which extends into said channel for providing a visual liquid condition indication adjacent said open end of said container means, terminal means on said inner member adjacent said open end of said container means, electrical lead wires extending from said light source and from said light detector to said terminal means and sealing means for sealing said container means and said inner member so as to prevent liquid from reaching said light source and said light detector.

2. A liquid condition indicating device as claimed in claim 1 wherein said container means and said inner member are of a general cylindrical shape.

3. A liquid condition indicating device as claimed in claim 1 wherein said inner member comprises one or more bore holes adjacent said open end of said container means.

4. A liquid condition indicating device as claimed in claim 3 wherein said inner member has an upper disc of a predetermined thickness and one or more wall portions that are thinner than said predetermined thickness with each of said wall portions being in alignment with one of said bores.

* * * * *